United States Patent [19]
Semenza

[11] Patent Number: 6,124,131
[45] Date of Patent: Sep. 26, 2000

[54] MUTANT HYPOXIA INDUCIBLE FACTOR-1 HIF-1

[75] Inventor: Gregg L. Semenza, Towson, Md.

[73] Assignee: The Johns Hopkins University School of Medicine, Baltimore, Md.

[21] Appl. No.: 09/148,547

[22] Filed: Aug. 25, 1998

[51] Int. Cl.$^7$ ............ C07K 16/00; C12N 15/12; C12N 15/74; C12N 15/85
[52] U.S. Cl. ............ 435/325; 435/69.1; 435/252.3; 435/320.1; 536/23.1; 536/23.5
[58] Field of Search ............ 435/320.1, 69.1, 435/325, 350, 7.1, 252.3; 530/350, 388.21; 424/93.1, 93.2, 93.21; 514/44; 536/23.1, 23.5

[56] References Cited

FOREIGN PATENT DOCUMENTS

WO 96/39426  12/1996  WIPO ............ C07K 1/00

OTHER PUBLICATIONS

Verma et al. Nature. 389: 239–241, Sep. 18, 1997.
Miller et al. FASEB. 9: 190–199, 1995.
Eck et al. Goodman and Gilman's The Pharmacological Basis of Therapeutics. NY: McGraw–Hill. Chap. 5, p. 81–82, 1995.
Fujiwara et al., Expressed Sequence Tag (EST), GenBank Accession Numbers D56430, D53682, R71408, T32121, HS14513, T32145, T35966, M85743, R71117, T32012, and Q60265. GenBank. May 30, 1995, see sequence alignments.
Benjamin et al., Activation of the Heat Shock Transcription Factor by Hypoxia in Mammalian Cells, Aug. 1990, Proceedings of the National Academy of Science USA, vol. 87, pp. 6263–6267.
Wang et al., Hypoxia–Inducible Factor 1 is a Basic–Helix–Loop–Helix–PAS Heterodimer Regulated by Cllular 02 Tension, Jun. 1995, Proceedings of the National Academy of Science USA, vol. 92, pp. 5510–5514.
Norris et al., Hypoxia–Induced Protein Binding to 02–Responsive Sequences on the Tyrosine Hydroxylase Gene, Oct. 6, 1995, Journal of Biological Chemistry, vol. 270, pp. 23774–23779.
Dejgaard et al., Identification, Molecular Cloning, Expression and Chromosome Mapping of a Family of Transformation Upregulated hnRNP–K Proteins Dervied by Alternative Splicing, 1994, J. Mol. Biol., vol. 236, pp. 33–48.

*Primary Examiner*—John L. LeGuyader
*Assistant Examiner*—Carrie Stroup
*Attorney, Agent, or Firm*—Gray Cary Ware & Freidenrich LLP; Lisa A. Haile

[57] ABSTRACT

Substantially purified stable human hypoxia-inducible factor-1α (sHIF-1α) mutein is provided. Polynucleotides encoding stable human hypoxia-inducible factor-1α mutein are also provided. A method is provided for treating a hypoxia-related tissue damage in a subject by administering to the subject a therapeutically effective amount of a sHIF-1α mutein or a nucleotide sequence including an expression control sequence operatively linked to a polynucleotide encoding a stable hypoxia-inducible factor-1α mutein. Formulations are provided for the administration of stable human hypoxia inducible factor-1α (HIF-1α) polypeptide or a polynucleotide encoding stable human hypoxia inducible factor-1α (HIF-1α) to a patient having hypoxia-related tissue damage.

18 Claims, 10 Drawing Sheets

| | | | | | | | | | |
|---|---|---|---|---|---|---|---|---|---|
|TAT|GTG|GAT|AGT|GAT|ATG|GTC|AAT|GAA|TTC|
|tyr|val|asp|ser|asp|met|val|asn|glu|phe|
|TTA|GCT|CCC|TAT|ATC|CCA|ATG|GAT|GAT|GAC|
|leu|ala|pro|tyr|ile|pro|met|asp|asp|asp|
|TTC|CAG|CAG|ACT|CAA|ATA|CAA|GAA|CCT|ACT|
|phe|gln|gln|thr|gln|ile|gln|glu|pro|thr|
|CCA|TCT|CCT|ACC|CAC|ATA|CAT|AAA|GAA|ACT|
|pro|ser|pro|thr|his|ile|his|lys|glu|thr|
|AAA|TCT|CAT|CCA|AGA|AGC|CCT|AAC|GTG|TTA|
|lys|ser|his|pro|arg|ser|pro|asn|cal|leu|
|ATG|GAA|CAT|GAT|GGT|TCA|CTT|TTT|CAA|GCA|
|met|glu|his|asp|gly|ser|leu|phe|gln|ala|
|GAA|CAG|AAT|GGA|ATG|GAG|CAA|AAG|ACA|ATT|
|glu|gln|asn|gly|met|glu|gln|lys|thr|ile|
|GTT|AAT|GCT|CCT|ATA|CAA|GGC|AGC|AGA|AAC|
|val|asn|ala|pro|ile|gln|gly|ser|arg|asn|

AGTCTATTTATATTTTCTACATCTAATTTTAGAAGCCTGG

TTTTTGGTATTTAAACCATTGCATTGCAGTAGCATCATT
CATAGGCAGTTGAAAATTTTTACACCTTTTTTTTCACA
TTAAGAAGAAATTTTTTTGGCCTATGAAATTGTTAAAC
GGCATTTATTTGGATAAAATTCTCAATTCAGAGAAATCA
GTATAAGATATTTTGAGCAGACTGTAAACAAGAAAAA
TAATTTTAGAAGCATTATTTTAGGAATATATAGTTGTCA
AAAAAAAAAAAAAAAAAAAAAAAAAAAAAAAAAAAA

FIG. 1A

```
GAG CCT AAT AGT CCC AGT GAA TAT TGT TTT
glu pro asn ser pro ser glu tyr sys phe
ACT CAG GAC ACA GAT TTA GAC TTG GAG ATG
thr gln asp thr asp leu asp leu glu met
AGC GCA AGT CCT CAA AGC ACA GTT ACA GTA
ser ala ser pro gln ser thr val thr val
ATG GAA GAC ATT AAA ATA TTG ATT GCA TCT
met glu asp ile lys ile leu ile ala ser
GCA GGA AAA GGA GTC ATA GAA CAG ACA GAA
ala gly lys gly val ile glu gln thr glu
GCT TTG CAG AAT GCT CAG AGA AAG CGA AAA
ala leu gln asn ala gln arg lys arg lys
TGG AAA CGT GTA AAA GGA TGC AAA TCT AGT
trp lys arg val lys gly cys lys ser ser
TTA CCA CAG CTG ACC AGT TAT GAT TGT GAA
leu pro gln leu thr ser tyr asp cys glu
CATTCCTTTTTTTGGACACTGGTGGCTCACTACCTAAAGC TGTTCTTTAATGCTGGATCACAGACAGCTCATTTTCTCAGT
AATATAATTTTTGTAAGAAGGCAGTAACCTTTCATCATGAT
AGTTACTCATGGAATATATTCTGCGTTTATAAACTAGTTT
TACATAATATAGAAGATATGCATATATCTAGAAGGTATGT
TGTAACTGATATTAAACCTAAATGTTCTGCCTACCCTGTTG
CTATTAACATCCTTTTTTTCATGTAGATTTCAATAATTGAG
ACTGTATTGTTTTGTTACATCAAATAAACATCTTCTGTGGA
```

FIG. 1B

```
TCC GAT GGA AGC ACT AGA CAA AGT TCA CCT
ser asp gly ser thr arg gln ser ser pro
GAA GAC ACA GAA GCA AAG AAC CCA TTT TCT
glu asp thr glu ala lys asn pro phe ser
CCA TTA GAA AGC AGT TCC GCA AGC CCT GAA
pro leu glu ser ser ser ala ser pro glu
GAT GAA TTA AAA ACA GTG ACA AAA GAC CGT
asp glu leu lys thr val thr lys asp arg
ACT CAA AGT CGG ACA GCC TCA CCA AAC AGA
thr gln ser arg thr ala ser pro asn arg
CCT GAG GAA GAA CTA AAT CCA AAG ATA CTA
pro glu glu glu leu asn pro lys ile leu
GAC GAT CAT GCA GCT ACT ACA TCA CTT TCT
asp asp his ala ala thr thr set leu ser
CTG CTG GGG CAA TCA ATG CAT GAA AGT GGA
leu leu gly gln ser met asp glu ser gly
TTG GAT CAA GTT AAC TGA GCTTTTTCTTAATTT
leu asp gln val asn OPA
CCCCTTTCTACTTAATTTACATTAATGCTCTTTTTTAGTA
GGAGTTTATCCCTTTTTCGAATTATTTTTAAGAAGATGCC
AGCCACAATTGCACAATATATTTTCTTAAAAAATACCAGC
AAATGCTGTATGGTTTATTATTTAAATGGGTAAAGCCATT
ACAATACCCTATGTAGTTGTGGAAGTTTATGCTAATATTG
TTTGCTCAAAATACAATGTTTGATTTATGCACTTTGTCG
TTTTCATTCCTTTTGCTCTTTGTGGTTGGATCTAACACTA
```

FIG. 1C

1502 CCC CAG ATT CAG GAT CAG ACA CCT AGT CCT
 492 pro gln ile gln asp gln thr pro ser pro
1622 AAG TTG GAA TTG GTA GAA AAA CTT TTT GCT
 532 lys leu glu leu val glu lys leu phe ala
1742 TTC CAG TTA CGT TCC TTC GAT CAG TTG TCA
 572 phe gln leu arg ser phe asp gln leu ser
1862 GCT AAT GCC ACC ACT ACC ACT GCC ACC ACT
 612 ala asn ala thr thr thr thr ala thr thr
1982 ACT AGT GCC ACA TCA TCA CCA TAT AGA GAT
 652 thr ser ala thr ser ser pro tyr arg asp
2102 TCT GTC GCT TTG AGT CAA AGA ACT ACA GTT
 692 ser val ala leu ser gln arg thr thr val
2222 GTA GGA ATT GGA ACA TTA TTA CAG CAG CCA
 732 val gly ile gly thr leu leu gln gln pro
2342 ATT TTA ATA CCC TCT GAT TTA GCA TGT AGA
 772 <u>ile leu ile pro ser asp leu ala cys arg</u>
2462 CTA CTG CAG GGT GAA GAA TTA CTC AGA GCT
 812 leu leu gln gly glu glu leu leu arg ala
2605 CTACAATACTGCACAAACTTGGTTAGTTCAATTTTTGAT
2764 TTAAAAAATGCACCTTTTTATTTATTTATTTTTGGCTAG
2923 TTTTACATAAATAATAATGCTTTGCCAGCAGTACGTGGT
3082 CTGGAACATGACATTGTTAATCATATAATAATGATTCTT
3241 TCTGATGTTTCTATAGTCACTTTGCCAGCTCAAAAGAAA
3400 AAAATCATGCATTCTTAGCAAAATTGCCTAGTATGTTAA
3559 CAGTAAATATCTTGTTTTTTCTATGTACATTGTACAAAT

FIG. 1D

```
GCG GGC GCC GGC GGC GCG AAC GAC AAG AAA
glu gly ala gly gly ala asn asp lys lys
CAT CAG TTG CCA CTT CCA CAT AAT GTG AGT
his gln leu pro leu pro his asn val ser
GAT GAC ATG AAA GCA CAG ATG AAT TGC TTT
asp asp met lys ala gln met asn cys phe
TTA ACT CAG TTT GAA CTA ACT GGA CAC AGT
leu thr gln phe glu leu thr gly his ser
AAC ACA CAG CGA AGC TTT TTT CTC AGA ATG
asn thr gln arg ser phe phe leu arg met
                   ___ ___ ___ ___
GAT ACC AAC AGT AAC CAA CCT CAG TGT GGG
asp thr asn ser asn gln pro gln cys gly
TTC CTC AGT CGA CAC AGC CTG GAT ATG AAA
phe leu ser arg his ser leu asp met lys
TTG GAC TCT GAT CAT CTG ACC AAA ACT CAT
leu asp ser asp his leu thr lys thr his
___ ___ ___ ___ ___ ___ ___
ACT GTC ATA TAT AAC ACC AAG AAT TCT CAA
thr val ile tyr asn thr lys asn ser gln
AAA CCG GTT GAA TCT TCA GAT ATG AAA ATG
lys pro val glu ser ser asp met lys met
CCA GCC GCT GGA GAC ACA ATC ATA TCT TTA
pro ala ala gly asp thr ile ile ser leu
AAA TTA CAG AAT ATA AAT TTG GCA ATG TCT
lys leu gln asn ile asn leu ala met ser
CCA GAG TCA CTG GAA CTT TCT TTT ACC ATG
pro glu ser leu glu leu ser phe thr met
```

FIG. 1E

```
                    GTGAAGACATCGCGGGGACCGATTCACC ATG
                                                 met
AAA GAA TCT GAA GTT TTT TAT GAG CTT GCT
lys glu ser glu val phe tyr glu leu ala
CTT CTG GAT GCT GGT GAT TTG GAT ATT GAA
leu leu asp ala gly asp leu asp ile glu
ATT TCT GAT AAT GTG AAC AAA TAC ATG GGA
ile ser asp asn val asn lys tyr met gly
AAT GGC CTT GTG AAA AAG GGT AAA GAA CAA
asn gly leu val lys lys gly lys glu glu
TTG CAC TGC ACA GGC CAC ATT CAC GTA TAT
leu his cys thr gly his ile his val tyr
AAT ATT GAA ATT CCT TTA GAT AGC AAG ACT
asn ile glu ile pro leu asp ser lys thr
GGC CGC TCA ATT TAT GAA TAT TAT CAT GCT
gly arg ser ile tyr glu tyr tyr his ala
GGT GGA TAT GTC TGG GTT GAA ACT CAA GCA
gly gly tyr val trp val glu thr gln ala
TTC TCC CTT CAA CAA ACA GAA TGT GTC CTT
phe ser leu gln gln thr glu cys val leu
AAG GAA CCT GAT GCT TTA ACT TTG CTG GCC
lys glu pro asp ala leu thr leu leu ala
AAT GAT GTA ATG CTC CCC TCA CCC AAC GAA
asn asp val met leu pro ser pro asn glu
CAA GAA GTT GCA TTA AAA TTA GAA CCA AAT
gln glu val ala leu lys leu glu pro asn
```

FIG. 1F

```
TCT CGA GAT GCA GCC AGA TCT CGG CGA AGT
ser arg asp ala ala arg ser arg arg ser
CTT ACC ATC AGC TAT TTG CGT GTG AGG AAA
leu thr ile ser tyr leu arg val arg lys
GTT CTC ACA GAT GAT GGT GAC ATG ATT TAC
val leu thr asp asp gly asp met ile tyr
GAG GAA ATG AGA GAA ATG CTT ACA CAC AGA
glu glu met arg glu met leu thr his arg
ATG AAC ATA AAG TCT GCA ACA TGG AAG GTA
met asn ile lys ser ala thr trp lys val
CTG ATT TGT GAA CCC ATT CCT CAC CCA TCA
leu ile cys glu pro ile pro his pro ser
TTG ATG GGA TAT GAG CCA GAA GAA CTT TTA
leu met gly tyr glu pro glu glu leu leu
ACA GGA CAG TAC AGG ATG CTT GCC AAA AGA
thr gly gln tyr arg met leu ala lys arg
GTG AGT GGT ATT ATT CAG CAC GAC TTG ATT
val ser gly ile ile gln his asp leu ile
GAT ACA AGT AGC CTC TTT GAC AAA CTT AAG
asp thr ser ser leu phe asp lys leu lys
GAC CAG CAA CTT GAG GAA GTA CCA TTA TAT
asp gln gln leu glu glu val pro leu tyr
CTT CGA AGT AGT GCT GAC CCT GCA CTC AAT
leu arg ser ser ala asp pro ala leu asn
```

*FIG. 1G*

```
   1
   1
  62  AAG  ATA  AGT  TCT  GAA  CGT  CGA  AAA  GAA  AAG
  12  lys  ile  ser  ser  glu  arg  arg  lys  glu  lys
 182  TCG  CAT  CTT  GAT  AAG  GCC  TCT  GTG  ATG  AGG
  52  ser  his  leu  asp  lys  ala  ser  val  met  arg
 302  TAT  TTG  AAA  GCC  TTG  GAT  GGT  TTT  GTT  ATG
  92  tyr  leu  lys  ala  leu  asp  gly  phe  val  met
 422  GTG  TTT  GAT  TTT  ACT  CAT  CCA  TGT  GAC  CAT
 132  val  phe  asp  phe  thr  his  pro  cys  asp  his
 542  AAG  TGT  ACC  CTA  ACT  AGC  CGA  GGA  AGA  ACT
 172  lys  cys  thr  leu  thr  ser  arg  gly  arg  thr
 662  TAT  AAG  AAA  CCA  CCT  ATG  ACC  TGC  TTG  GTG
 212  tyr  lys  lys  pro  pro  met  thr  cys  leu  val
 782  TTT  TCT  TAT  TGT  GAT  GAA  AGA  ATT  ACC  GAA
 252  phe  ser  tyr  cys  asp  glu  arg  ile  thr  glu
 902  CAT  GAT  ATG  TTT  ACT  AAA  GGA  CAA  GTC  ACC
 292  his  asp  met  phe  thr  lys  gly  gln  val  thr
1022  CCA  CAG  TGC  ATT  GTA  TGT  GTG  AAT  TAC  GTT
 332  pro  gln  cys  ile  val  cys  val  asn  tyr  val
1142  ACT  CAG  CTA  TTC  ACC  AAA  GTT  GAA  TCA  GAA
 372  thr  gln  leu  phe  thr  lys  val  glu  ser  glu
1262  GAT  TTT  GGC  AGC  AAC  GAC  ACA  GAA  ACT  GAT
 412  asp  phe  gly  ser  asn  asp  thr  glu  thr  asp
1382  CCA  TTA  CCC  ACC  GCT  GAA  ACG  CCA  AAG  CCA
 452  pro  leu  pro  thr  ala  glu  thr  pro  lys  pro
```

FIG. 1H

| | RESIDUES | REGULATION |
|---|---|---|
| ←bHLH-PAS→ ←TADs→ | 1-826 | + |
| | 1-754 | + |
| | 1-729 | + |
| | 1-726 | + |
| | 1-703 | - |
| | 1-681 | - |
| | 1-608 | - |
| | 1-390 | - |

| | RESIDUES | REGULATION | |
|---|---|---|---|
| ←bHLH-PAS→ ←TADs→ | | Wt | mut |
| | 1-826 | + | + |
| | 1-390 | - | |
| | 1-391, 429-826 | + | - |
| | 1-391, 469-826 | + | - |
| | 1-391, 494-826 | + | - |
| | 1-391, 508-826 | + | - |
| | 1-391, 512-826 | + | - |
| | 1-391, 517-826 | + | - |
| | 1-391, 521-826 | - | |
| | 1-391, 549-826 | - | |
| | 1-391, 576-826 | - | |

SEQUENCE LISTING

```
<160> NUMBER OF SEQ ID NOS: 2

<210> SEQ ID NO 1
<211> LENGTH: 3736
<212> TYPE: DNA
<213> ORGANISM: Homo sapiens
<220> FEATURE:
<221> NAME/KEY: CDS
<222> LOCATION: (29)..(2509)

<400> SEQUENCE: 1
gtgaagacat cgcggggacc gattcacc atg gag ggc gcc ggc ggc gcg aac         52
                                Met Glu Gly Ala Gly Gly Ala Asn
                                 1               5
```

```
gac aag aaa aag ata agt tct gaa cgt cga aaa gaa aag tct cga gat      100
Asp Lys Lys Lys Ile Ser Ser Glu Arg Arg Lys Glu Lys Ser Arg Asp
    10              15                  20 gca gcc aga tct cgg cga agt aaa gaa tct gaa gtt ttt tat gag ctt      148
Ala Ala Arg Ser Arg Arg Ser Lys Glu Ser Glu Val Phe Tyr Glu Leu
25              30                  35                      40 gct cat cag ttg cca ctt cca cat aat gtg agt tcg cat ctt gat aag      196
Ala His Gln Leu Pro Leu Pro His Asn Val Ser Ser His Leu Asp Lys
                    45                  50                  55 gcc tct gtg atg agg ctt acc atc agc tat ttg cgt gtg agg aaa ctt      244
Ala Ser Val Met Arg Leu Thr Ile Ser Tyr Leu Arg Val Arg Lys Leu
            60                  65                  70 ctg gat gct ggt gat ttg gat att gaa gat gac atg aaa gca cag atg      292
Leu Asp Ala Gly Asp Leu Asp Ile Glu Asp Asp Met Lys Ala Gln Met
        75                  80                  85 aat tgc ttt tat ttg aaa gcc ttg gat ggt ttt gtt atg gtt ctc aca      340
Asn Cys Phe Tyr Leu Lys Ala Leu Asp Gly Phe Val Met Val Leu Thr
    90                  95                  100 gat gat ggt gac atg att tac att tct gat aat gtg aac aaa tac atg      388
Asp Asp Gly Asp Met Ile Tyr Ile Ser Asp Asn Val Asn Lys Tyr Met
105             110                 115                 120 gga tta act cag ttt gaa cta act gga cac agt gtg ttt gat ttt act      436
Gly Leu Thr Gln Phe Glu Leu Thr Gly His Ser Val Phe Asp Phe Thr
                125                 130                 135 cat cca tgt gac cat gag gaa atg aga gaa atg ctt aca cac aga aat      484
His Pro Cys Asp His Glu Glu Met Arg Glu Met Leu Thr His Arg Asn
            140                 145                 150 ggc ctt gtg aaa aag ggt aaa gaa caa aac aca cag cga agc ttt ttt      532
Gly Leu Val Lys Lys Gly Lys Glu Gln Asn Thr Gln Arg Ser Phe Phe
        155                 160                 165 ctc aga atg aag tgt acc cta act agc cga gga aga act atg aac ata      580
Leu Arg Met Lys Cys Thr Leu Thr Ser Arg Gly Arg Thr Met Asn Ile
170                 175                 180 aag tct gca aca tgg aag gta ttg cac tgc aca ggc cac att cac gta      628
Lys Ser Ala Thr Trp Lys Val Leu His Cys Thr Gly His Ile His Val
185                 190                 195                 200 tat gat acc aac agt aac caa cct cag tgt ggg tat aag aaa cca cct      676
Tyr Asp Thr Asn Ser Asn Gln Pro Gln Cys Gly Tyr Lys Lys Pro Pro
                205                 210                 215 atg acc tgc ttg gtg ctg att tgt gaa ccc att cct cac cca tca aat      724
Met Thr Cys Leu Val Leu Ile Cys Glu Pro Ile Pro His Pro Ser Asn
            220                 225                 230 att gaa att cct tta gat agc aag act ttc ctc agt cga cac agc ctg      772
Ile Glu Ile Pro Leu Asp Ser Lys Thr Phe Leu Ser Arg His Ser Leu
        235                 240                 245 gat atg aaa ttt tct tat tgt gat gaa aga att acc gaa ttg atg gga      820
Asp Met Lys Phe Ser Tyr Cys Asp Glu Arg Ile Thr Glu Leu Met Gly
250                 255                 260 tat gag cca gaa gaa ctt tta ggc cgc tca att tat gaa tat tat cat      868
Tyr Glu Pro Glu Glu Leu Leu Gly Arg Ser Ile Tyr Glu Tyr Tyr His
265                 270                 275                 280 gct ttg gac tct gat cat ctg acc aaa act cat cat gat atg ttt act      916
Ala Leu Asp Ser Asp His Leu Thr Lys Thr His His Asp Met Phe Thr
                285                 290                 295 aaa gga caa gtc acc aca gga cag tac agg atg ctt gcc aaa aga ggt      964
Lys Gly Gln Val Thr Thr Gly Gln Tyr Arg Met Leu Ala Lys Arg Gly
            300                 305                 310 gga tat gtc tgg gtt gaa act caa gca act gtc ata tat aac acc aag      1012
Gly Tyr Val Trp Val Glu Thr Gln Ala Thr Val Ile Tyr Asn Thr Lys
        315                 320                 325
```

-continued

| | | |
|---|---|---|
| aat tct caa cca cag tgc att gta tgt gtg aat tac gtt gtg agt ggt<br>Asn Ser Gln Pro Gln Cys Ile Val Cys Val Asn Tyr Val Val Ser Gly<br>330                     335                     340 | 1060 |
| att att cag cac gac ttg att ttc tcc ctt caa caa aca gaa tgt gtc<br>Ile Ile Gln His Asp Leu Ile Phe Ser Leu Gln Gln Thr Glu Cys Val<br>345                     350                     355                     360 | 1108 |
| ctt aaa ccg gtt gaa tct tca gat atg aaa atg act cag cta ttc acc<br>Leu Lys Pro Val Glu Ser Ser Asp Met Lys Met Thr Gln Leu Phe Thr<br>365                     370                     375 | 1156 |
| aaa gtt gaa tca gaa gat aca agt agc ctc ttt gac aaa ctt aag aag<br>Lys Val Glu Ser Glu Asp Thr Ser Ser Leu Phe Asp Lys Leu Lys Lys<br>380                     385                     390 | 1204 |
| gaa cct gat gct tta act ttg ctg gcc cca gcc gct gga gac aca atc<br>Glu Pro Asp Ala Leu Thr Leu Leu Ala Pro Ala Ala Gly Asp Thr Ile<br>395                     400                     405 | 1252 |
| ata tct tta gat ttt ggc agc aac gac aca gaa act gat gac cag caa<br>Ile Ser Leu Asp Phe Gly Ser Asn Asp Thr Glu Thr Asp Asp Gln Gln<br>410                     415                     420 | 1300 |
| ctt gag gaa gta cca tta tat aat gat gta atg ctc ccc tca ccc aac<br>Leu Glu Glu Val Pro Leu Tyr Asn Asp Val Met Leu Pro Ser Pro Asn<br>425                     430                     435                     440 | 1348 |
| gaa aaa tta cag aat ata aat ttg gca atg tct cca tta ccc acc gct<br>Glu Lys Leu Gln Asn Ile Asn Leu Ala Met Ser Pro Leu Pro Thr Ala<br>445                     450                     455 | 1396 |
| gaa acg cca aag cca ctt cga agt agt gct gac cct gca ctc aat caa<br>Glu Thr Pro Lys Pro Leu Arg Ser Ser Ala Asp Pro Ala Leu Asn Gln<br>460                     465                     470 | 1444 |
| gaa gtt gca tta aaa tta gaa cca aat cca gag tca ctg gaa ctt tct<br>Glu Val Ala Leu Lys Leu Glu Pro Asn Pro Glu Ser Leu Glu Leu Ser<br>475                     480                     485 | 1492 |
| ttt acc atg ccc cag att cag gat cag aca cct agt cct tcc gat gga<br>Phe Thr Met Pro Gln Ile Gln Asp Gln Thr Pro Ser Pro Ser Asp Gly<br>490                     495                     500 | 1540 |
| agc act aga caa agt tca cct gag cct aat agt ccc agt gaa tat tgt<br>Ser Thr Arg Gln Ser Ser Pro Glu Pro Asn Ser Pro Ser Glu Tyr Cys<br>505                     510                     515                     520 | 1588 |
| ttt tat gtg gat agt gat atg gtc aat gaa ttc aag ttg gaa ttg gta<br>Phe Tyr Val Asp Ser Asp Met Val Asn Glu Phe Lys Leu Glu Leu Val<br>525                     530                     535 | 1636 |
| gaa aaa ctt ttt gct gaa gac aca gaa gca aag aac cca ttt tct act<br>Glu Lys Leu Phe Ala Glu Asp Thr Glu Ala Lys Asn Pro Phe Ser Thr<br>540                     545                     550 | 1684 |
| cag gac aca gat tta gac ttg gag atg tta gct ccc tat atc cca atg<br>Gln Asp Thr Asp Leu Asp Leu Glu Met Leu Ala Pro Tyr Ile Pro Met<br>555                     560                     565 | 1732 |
| gat gat gac ttc cag tta cgt tcc ttc gat cag ttg tca cca tta gaa<br>Asp Asp Asp Phe Gln Leu Arg Ser Phe Asp Gln Leu Ser Pro Leu Glu<br>570                     575                     580 | 1780 |
| agc agt tcc gca agc cct gaa agc gca agt cct caa agc aca gtt aca<br>Ser Ser Ser Ala Ser Pro Glu Ser Ala Ser Pro Gln Ser Thr Val Thr<br>585                     590                     595                     600 | 1828 |
| gta ttc cag cag act caa ata caa gaa cct act gct aat gcc acc act<br>Val Phe Gln Gln Thr Gln Ile Gln Glu Pro Thr Ala Asn Ala Thr Thr<br>605                     610                     615 | 1876 |
| acc act gcc acc act gat gaa tta aaa aca gtg aca aaa gac cgt atg<br>Thr Thr Ala Thr Thr Asp Glu Leu Lys Thr Val Thr Lys Asp Arg Met<br>620                     625                     630 | 1924 |
| gaa gac att aaa ata ttg att gca tct cca tct cct acc cac ata cat<br>Glu Asp Ile Lys Ile Leu Ile Ala Ser Pro Ser Pro Thr His Ile His | 1972 |

|     |     | 635 |     |     |     |     | 640 |     |     |     |     | 645 |     |     |      |
|-----|-----|-----|-----|-----|-----|-----|-----|-----|-----|-----|-----|-----|-----|-----|------|
| aaa | gaa | act | act | agt | gcc | aca | tca | tca | cca | tat | aga | gat | act | caa agt | 2020 |
| Lys | Glu | Thr | Thr | Ser | Ala | Thr | Ser | Ser | Pro | Tyr | Arg | Asp | Thr | Gln Ser |      |
|     |     | 650 |     |     |     |     | 655 |     |     |     |     | 660 |     |     |      | cgg aca gcc tca cca aac aga gca gga aaa gga gtc ata gaa cag aca    2068
Arg Thr Ala Ser Pro Asn Arg Ala Gly Lys Gly Val Ile Glu Gln Thr
665                 670                 675                 680 gaa aaa tct cat cca aga agc cct aac gtg tta tct gtc gct ttg agt    2116
Glu Lys Ser His Pro Arg Ser Pro Asn Val Leu Ser Val Ala Leu Ser
            685                 690                 695 caa aga act aca gtt cct gag gaa gaa cta aat cca aag ata cta gct    2164
Gln Arg Thr Thr Val Pro Glu Glu Glu Leu Asn Pro Lys Ile Leu Ala
        700                 705                 710 ttg cag aat gct cag aga aag cga aaa atg gaa cat gat ggt tca ctt    2212
Leu Gln Asn Ala Gln Arg Lys Arg Lys Met Glu His Asp Gly Ser Leu
    715                 720                 725 ttt caa gca gta gga att gga aca tta tta cag cag cca gac gat cat    2260
Phe Gln Ala Val Gly Ile Gly Thr Leu Leu Gln Gln Pro Asp Asp His
730                 735                 740 gca gct act aca tca ctt tct tgg aaa cgt gta aaa gga tgc aaa tct    2308
Ala Ala Thr Thr Ser Leu Ser Trp Lys Arg Val Lys Gly Cys Lys Ser
745                 750                 755                 760 agt gaa cag aat gga atg gag caa aag aca att att tta ata ccc tct    2356
Ser Glu Gln Asn Gly Met Glu Gln Lys Thr Ile Ile Leu Ile Pro Ser
            765                 770                 775 gat tta gca tgt aga ctg ctg ggg caa tca atg gat gaa agt gga tta    2404
Asp Leu Ala Cys Arg Leu Leu Gly Gln Ser Met Asp Glu Ser Gly Leu
        780                 785                 790 cca cag ctg acc agt tat gat tgt gaa gtt aat gct cct ata caa ggc    2452
Pro Gln Leu Thr Ser Tyr Asp Cys Glu Val Asn Ala Pro Ile Gln Gly
    795                 800                 805 agc aga aac cta ctg cag ggt gaa gaa tta ctc aga gct ttg gat caa    2500
Ser Arg Asn Leu Leu Gln Gly Glu Glu Leu Leu Arg Ala Leu Asp Gln
810                 815                 820 gtt aac tga gcttttctt aatttcattc ctttttttgg acactggtgg    2549
Val Asn
825 ctcactacct aaagcagtct atttatattt tctacatcta attttagaag cctggctaca    2609 atactgcaca aacttggtta gttcaatttt tgatccccctt tctacttaat ttacattaat    2669 gctcttttt agtatgttct ttaatgctgg atcacagaca gctcattttc tcagtttttt    2729 ggtatttaaa ccattgcatt gcagtagcat cattaattaa aaaatgcacc ttttttattta    2789 tttatttttg gctagggagt ttatcccttt ttcgaattat ttttaagaag atgccaatat    2849 aattttgta agaaggcagt aacctttcat catgatcata ggcagttgaa aaatttttac    2909 acctttttt tcacaaattt tacataaata ataatgcttt gccagcagta cgtggtagcc    2969 acaattgcac aatatatttt cttaaaaaat accagcagtt actcatggaa tatattctgc    3029 gtttataaaa ctagttttta agaagaaatt ttttttggcc tatgaaattg ttaaacaact    3089 ggaacatgac attgttaatc atataataat gattcttaaa tgctgtatgg tttattattt    3149 aaatgggtaa agccatttac ataatataga aagatatgca tatatctaga aggtatgtgg    3209 catttatttg gataaaattc tcaattcaga gaaatcaaat ctgatgtttc tatagtcact    3269 ttgccagctc aaaagaaaac aatacccctat gtagttgtgg aagtttatgc taatattgtg    3329 taactgatat taaacctaaa tgttctgcct accctgttgg tataaagata ttttgagcag    3389 actgtaaaca agaaaaaaaa aaaatcatgc attcttagca aaattgccta gtatgttaat    3449

-continued

```
ttgctcaaaa tacaatgttt gattttatgc actttgtcgc tattaacatc ctttttttca    3509
tgtagatttc aataattgag taattttaga agcattattt taggaatata tagttgtcaa    3569
aaacagtaaa tatcttgttt tttctatgta cattgtacaa attttttcatt ccttttgctc   3629 tttgtggttg gatctaacac taactgtatt gttttgttac atcaaataaa catcttctgt    3689
ggaaaaaaaa aaaaaaaaaa aaaaaaaaaa aaaaaaaaaa aaaaaaa                  3736
```

<210> SEQ ID NO 2
<211> LENGTH: 826
<212> TYPE: PRT
<213> ORGANISM: Homo sapiens

<400> SEQUENCE: 2

```
Met Glu Gly Ala Gly Gly Ala Asn Asp Lys Lys Lys Ile Ser Ser Glu
 1               5                  10                  15

Arg Arg Lys Glu Lys Ser Arg Asp Ala Ala Arg Ser Arg Arg Ser Lys
             20                  25                  30

Glu Ser Glu Val Phe Tyr Glu Leu Ala His Gln Leu Pro Leu Pro His
         35                  40                  45

Asn Val Ser Ser His Leu Asp Lys Ala Ser Val Met Arg Leu Thr Ile
     50                  55                  60

Ser Tyr Leu Arg Val Arg Lys Leu Leu Asp Ala Gly Asp Leu Asp Ile
 65                  70                  75                  80

Glu Asp Asp Met Lys Ala Gln Met Asn Cys Phe Tyr Leu Lys Ala Leu
                 85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320
```

-continued

```
Ala Thr Val Ile Tyr Asn Thr Lys Asn Ser Gln Pro Gln Cys Ile Val
                325                 330                 335
Cys Val Asn Tyr Val Val Ser Gly Ile Ile Gln His Asp Leu Ile Phe
            340                 345                 350
Ser Leu Gln Gln Thr Glu Cys Val Leu Lys Pro Val Glu Ser Ser Asp
        355                 360                 365
Met Lys Met Thr Gln Leu Phe Thr Lys Val Glu Ser Glu Asp Thr Ser
    370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
                405                 410                 415
Asp Thr Glu Thr Asp Asp Gln Gln Leu Glu Glu Val Pro Leu Tyr Asn
            420                 425                 430
Asp Val Met Leu Pro Ser Pro Asn Glu Lys Leu Gln Asn Ile Asn Leu
        435                 440                 445
Ala Met Ser Pro Leu Pro Thr Ala Glu Thr Pro Lys Pro Leu Arg Ser
    450                 455                 460
Ser Ala Asp Pro Ala Leu Asn Gln Glu Val Ala Leu Lys Leu Glu Pro
465                 470                 475                 480
Asn Pro Glu Ser Leu Glu Leu Ser Phe Thr Met Pro Gln Ile Gln Asp
                485                 490                 495
Gln Thr Pro Ser Pro Ser Asp Gly Ser Thr Arg Gln Ser Ser Pro Glu
            500                 505                 510
Pro Asn Ser Pro Ser Glu Tyr Cys Phe Tyr Val Asp Ser Asp Met Val
        515                 520                 525
Asn Glu Phe Lys Leu Glu Leu Val Glu Lys Leu Phe Ala Glu Asp Thr
    530                 535                 540
Glu Ala Lys Asn Pro Phe Ser Thr Gln Asp Thr Asp Leu Asp Leu Glu
545                 550                 555                 560
Met Leu Ala Pro Tyr Ile Pro Met Asp Asp Asp Phe Gln Leu Arg Ser
                565                 570                 575
Phe Asp Gln Leu Ser Pro Leu Glu Ser Ser Ser Ala Ser Pro Glu Ser
            580                 585                 590
Ala Ser Pro Gln Ser Thr Val Thr Val Phe Gln Gln Thr Gln Ile Gln
        595                 600                 605
Glu Pro Thr Ala Asn Ala Thr Thr Thr Thr Ala Thr Thr Asp Glu Leu
    610                 615                 620
Lys Thr Val Thr Lys Asp Arg Met Glu Asp Ile Lys Ile Leu Ile Ala
625                 630                 635                 640
Ser Pro Ser Pro Thr His Ile His Lys Glu Thr Thr Ser Ala Thr Ser
                645                 650                 655
Ser Pro Tyr Arg Asp Thr Gln Ser Arg Thr Ala Ser Pro Asn Arg Ala
            660                 665                 670
Gly Lys Gly Val Ile Glu Gln Thr Glu Lys Ser His Pro Arg Ser Pro
        675                 680                 685
Asn Val Leu Ser Val Ala Leu Ser Gln Arg Thr Thr Val Pro Glu Glu
    690                 695                 700
Glu Leu Asn Pro Lys Ile Leu Ala Leu Gln Asn Ala Gln Arg Lys Arg
705                 710                 715                 720
Lys Met Glu His Asp Gly Ser Leu Phe Gln Ala Val Gly Ile Gly Thr
                725                 730                 735
Leu Leu Gln Gln Pro Asp Asp His Ala Ala Thr Thr Ser Leu Ser Trp
```

```
                    740                     745                     750
Lys Arg Val Lys Gly Cys Lys Ser Ser Glu Gln Asn Gly Met Glu Gln
            755                     760                     765

Lys Thr Ile Ile Leu Ile Pro Ser Asp Leu Ala Cys Arg Leu Leu Gly
    770                     775                     780

Gln Ser Met Asp Glu Ser Gly Leu Pro Gln Leu Thr Ser Tyr Asp Cys
785                     790                     795                 800

Glu Val Asn Ala Pro Ile Gln Gly Ser Arg Asn Leu Leu Gln Gly Glu
                805                     810                     815

Glu Leu Leu Arg Ala Leu Asp Gln Val Asn
            820                     825
```

MUTANT HYPOXIA INDUCIBLE FACTOR-1 HIF-1

STATEMENT AS TO FEDERALLY SPONSORED RESEARCH

This invention was made in part with funds from the National Heart, Lung, and Blood Institute, grant number 1R01-HL55338. The government may have certain rights in this invention.

FIELD OF THE INVENTION

This invention relates generally to hypoxia-related proteins and more specifically to DNA-binding proteins which are stable under non-hypoxic and hypoxic conditions.

BACKGROUND OF THE INVENTION

Mammals require molecular oxygen ($O_2$) for essential metabolic processes including oxidative phosphorylation in which $O_2$ serves as electron acceptor during ATP formation. Systemic, local, and intracellular homeostatic responses elicited by hypoxia (the state in which $O_2$ demand exceeds supply) include erythropoiesis by individuals who are anemic or at high altitude (Jelkmann, *Physiol. Rev.* 72:449–489, 1992), neovascularization in ischemic myocardium (White et al., *Circ. Res.* 71:1490–1500, 1992), and glycolysis in cells cultured at reduced $O_2$ tension (Wolfe et al., *Eur. J. Biochem.* 135:405–412, 1983). These adaptive responses either increase $O_2$ delivery or activate alternate metabolic pathways that do not require $O_2$. Hypoxia-inducible gene products that participate in these responses include erythropoietin (EPO) (reviewed in Semenza, *Hematol. Oncol. Clinics N. Amer.* 8:863–884, 1994), vascular endothelial growth factor (Shweiki et al., *Nature* 359:843–845, 1992; Banai et al., *Cardiovasc. Res.* 28:1176–1179, 1994; Goldberg & Schneider, *J. Biol. Chem.* 269:4355–4359, 1994), and glycolytic enzymes (Firth et al., *Proc. Natl. Acad. Sci. USA* 91:6496–6500, 1994; Semenza et al., *J. Biol. Chem.* 269:23757–23763, 1994).

The molecular mechanisms that mediate genetic responses to hypoxia have been extensively investigated for the EPO gene, which encodes a growth factor that regulates erythropoiesis and thus blood $O_2$-carrying capacity (Jelkmann, 1992, supra; Semenza, 1994, supra). Cis-acting DNA sequences required for transcriptional activation in response to hypoxia were identified in the EPO 3'-flanking region and a trans-acting factor that binds to the enhancer, hypoxia-inducible factor 1 (HIF-1), fulfilled criteria for a physiological regulator of EPO transcription. In particular, inducers of EPO expression (1% $O_2$, cobalt chloride [$CoCl_2$], and desferrioxamine [DFX]) also induced HIF-1 DNA binding activity with similar kinetics. In addition, inhibitors of EPO expression (actinomycin D, cycloheximide, and 2-aminopurine) blocked induction of HIF-1 activity. Furthermore, mutations in the EPO 3'-flanking region that eliminated HIF-1 binding also eliminated enhancer function (Semenza, 1994, supra). These results also support the hypothesis that $O_2$ tension is sensed by a hemoprotein (Goldberg et al., *Science* 242:1412–1415, 1988) and that a signal transduction pathway requiring ongoing transcription, translation, and protein phosphorylation participates in the induction of HIF-1 DNA-binding activity and EPO transcription in hypoxic cells (Semenza, 1994, supra).

EPO expression is cell type specific, but induction of HIF-1 activity by 1% $O_2$, $CoCl_2$, or DFX was detected in many mammalian cell lines (Wang & Semenza, *Proc. Natl. Acad. Sci. USA* 90:4304–4308, 1993). The EPO enhancer directed hypoxia-inducible transcription of reporter genes transfected into non-EPO-producing cells (Wang & Semenza, 1993, supra; Maxwell et al., *Proc. Natl. Acad. Sci. USA* 90:2423–2427, 1993). RNAs encoding several glycolytic enzymes were induced by 1% $O_2$, $CoCl_2$, or DFX in EPO-producing Hep3B or nonproducing HeLa cells whereas cycloheximide blocked their induction and glycolytic gene sequences containing HIF-1 binding sites mediated hypoxia-inducible transcription in transfection assays (Firth et al., 1994, supra; Semenza et al., 1994, supra). These experiments support the role of HIF-1 in activating homeostatic responses to hypoxia.

Hypoxia inducible factor-1 (HIF-1) is a mammalian transcription factor expressed uniquely in response to physiologically relevant levels of hypoxia (Wang, G. L., et al., *Proc. Natl. Acad. Sci. USA* 92:5510–5514, 1995; Wang, G. L., and Semenza, G. L., *J. Biol. Chem.* 270:1230–1237, 1995). HIF-1 is a basic helix loop-helix protein that binds to cis-acting hypoxia-responsive elements of genes induced by hypoxia (Wang, G. L., and Semenza, G. L., *Curr. Opin. Hematol.* 3:156–162, 1992; Jiang, B. H., et al., *J. Biol. Chem.* 272:19253–19260, 1997). The genes that are activated by HIF-1 in cells subjected to hypoxia include EPO, vascular endothelial growth hormone (VEGF), heme oxygenase-1, inducible nitric oxide synthase, and glycolytic enzymes aldolase A, enolase 1, lactate dehydrogenase A, phosphofructokinase I, and phosphoglycerate kinase 1 (Semenza, G. L., et al., *Kid. Int.* 51:553–555, 1997). HIF-1 DNA binding activity and HIF-1 protein concentration increases exponentially as cells are subjected to decreasing $O_2$ concentrations (Jiang, B. H., et al., *Am J. Physiol.* 271:C1172–C1180, 1996).

HIF-1 is a heterodimer of two subunits, HIF-1α and HIF-1β. The HIF-1α subunit is unique to HIF-1, whereas HIF-1β (also known as aryl hydrocarbon receptor nuclear translocator, ARNT) can dimerize with other proteins. The concentration of HIF-1α and HIF-1β RNA and HIF-1α and HIF-1β polypeptide increases in cells exposed to hypoxic conditions (Wiener, C. M., et al., *Biochem. Biophys. Res. Commun.* 225:485–488, 1996).

Structural analysis of HIF-1α revealed that dimerization requires two domains, termed HLH and PAS. DNA binding is mediated by a basic domain (Semenza, G. L., et al., *Kid. Int.* 51:553–555, 1997). Two transactivation domains are contained in HIF-1α, located between amino acids 531 and 826. The minimal transactivation domains are at amino acid residues 531–575 and 786–826 (Jiang, B. H., et al., 1997, supra; Semenza, G. L., et al., 1997, supra). Amino acids 1–166 are key in mediating heterodimerization with HIF-1β (ARNT), but amino acids 1–390 are required for optimal DNA binding. In addition, deletion of the carboxy terminus of HIF-1α (amino acids 391–826) decreased the ability of HIF-1 to activate transcription. However, HIF-1α (1–390) was expressed at high levels in both hypoxic and non-hypoxic cells in contrast to full-length HIF-1α (1–826) which was expressed at much higher levels in hypoxic relative to non-hypoxic cells (Jiang, B.-H., et al., *J. Biol. Chem.* 271:17771–17778, 1996).

SUMMARY OF THE INVENTION

This invention is based on the discovery and isolation of unique variant forms of HIF-1α polypeptide that are stable under hypoxic and nonhypoxic conditions.

In one embodiment, the invention provides a substantially purified polypeptide having a sequence as set forth in SEQ ID NO:22 wherein amino acids 392 to 428 are deleted therefrom, amino acid 551 is changed from a serine to any other amino acid, and amino acid 552 is changed from a threonine to any other amino acid. Isolated polynucleotides encoding such a polypeptide as well as antibodies which preferentially bind this polypeptide are also provided in a particular embodiment, serine 551 is changed to glycine and threonine 552 to alanine.

In one embodiment, a method is provided for treating a hypoxia-related tissue damage in a subject, by administering to the subject a therapeutically effective amount of a nucleotide sequence comprising an expression control sequence operatively linked to a polynucleotide encoding a polypeptide having a sequence as set forth in SEQ ID NO:1, wherein amino acids 392 to 428 are deleted therefrom, amino acid 551 is changed from a serine to any other amino acid, and amino acid 552 is changed from a threonine to any other amino acid.

In another embodiment, the invention provides a method of treating a hypoxia-related tissue damage in a subject by administering to the subject a therapeutically effective amount of a polypeptide having a sequence as set forth in SEQ ID NO:1, wherein amino acids 392 to 428 are deleted therefrom, amino acid 551 is changed from a serine to any other amino acid, and amino acid 552 is changed from a threonine to any other amino acid.

In a further embodiment, the invention provides a formulation for administration of stable human hypoxia inducible factor-1α (HIF-1α) polypeptide to a patient having hypoxia related tissue damage. The method includes a substantially pure polypeptide having a sequence as set forth in SEQ ID NO:1, wherein amino acids 392 to 428 are deleted therefrom, amino acid 551 is changed from a serine to any other amino acid, and amino acid 552 is changed from a threonine to any other amino acid; and a pharmaceutically acceptable carrier.

The invention also provides a formulation for administration of a polynucleotide encoding stable human hypoxia inducible factor-1α (HIF-1α) to a patient having hypoxia related tissue damage, including a therapeutically effective amount of a nucleic acid sequence comprising an expression control sequence operatively linked to a polynucleotide encoding a polypeptide having a sequence as set forth in SEQ ID NO:1, wherein amino acids 392 to 428 are deleted therefrom, amino acid 551 is changed from a serine to any other amino acid, and amino acid 552 is changed from a threonine to any other amino acid; and a pharmaceutically acceptable carrier.

BRIEF DESCRIPTION OF THE DRAWINGS

FIG. 1 is the amino acid sequence (SEQ ID NO:2) and nucleotide sequence (SEQ ID NO:1) of wild-type HIF-1α.

DETAILED DESCRIPTION OF THE INVENTION

Figures 2, 3, 4:
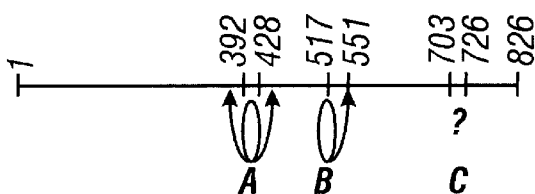
FIG. 2 shows an analysis of the effect of carboxyl-terminal deletions on the regulated expression of HIF-1α.
FIG. 3 shows an analysis of the effect of internal deletions on regulated expression of HIF-1α polypeptide. Oxygen regulation of the HIF-1α polypeptide containing the indicated internal deletion is shown in the "wt" column, where a "+" indicates that the polypeptide is regulated, and is therefore unstable under non-hypoxic conditions. Each of the indicated internal deletions in HIF-1α has been combined with a double point mutation (a serine to glycine mutation at amino acid 551 and a threonine to alanine mutation at residue 552). The oxygen regulation of the polypeptide containing both the indicated internal deletion and the double point mutation is shown in the "mut" column, where a "+" indicates that the polypeptide is regulated, and is therefore unstable under non-hypoxic conditions.
FIG. 4 shows a model of regulated expression of HIF-1α. Putative regulatory sequences identified within the HIF-1α protein by deletion analysis are indicated. Potential interactions with regulatory proteins such as a phosphatase, kinase, or protease are also shown.

It must be noted that as used herein and in the appended claims, the singular forms "a," "and," and "the" include plural referents unless the context clearly dictates otherwise. Thus, for example, reference to "a cell" includes a plurality of such cells and reference to "the plasmid" includes reference to one or more plasmids and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the cell lines, vectors, and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The invention provides a substantially pure stable hypoxia-inducible factor-1α (sHIF-1α) mutein. Wild-type, full-length HIF-1α is expressed at lower levels in nonhypoxic cells as compared to hypoxic cells (Wang, G. L., et al., Proc. Natl. Acad. Sci. USA 92:5510–5514, 1995; Wang, G. L., and Semenza, S. L., J. Biol. Chem. 270:1230–1237, 1995; Wang, G. L., and Semenza, S. L., Curr. Opin. Hematol. 3:156–162, 1992; Jiang, B. H., et al., J. Biol. Chem. 272:19253–19260, 1997, herein incorporated by reference) while sHIF-1α is stable under nonhypoxic as well as hypoxic conditions. Wild type HIF-1α and sHIF-1α are characterized as being able to form heterodimers with HIF-1β to form a DNA-binding protein, hypoxia inducible factor-1 (HIF-1), a mammalian transcription factor. HIF-1 activates erythropoietin (EPO), vascular endothelial growth factor (VEGF), and glycolytic gene transcription.

POLYNUCLEOTIDES AND POLYPEPTIDES

The term "mutein" as used herein refers to a variant form of HIF-1α polypeptide. HIF-1α polypeptide, upon dimerization with HIF-1β, is a DNA binding protein, which is characterized as activating structural gene expression where the promoter region of the structural gene contains a HIF-1 binding site (Semenza, G. L., et al., *Kid. Int.* 51:553–555, 1997; Iyer, N. V., et al., *Genes Dev.* 12:149–162, 1998, both herein incorporated by reference). Examples of such structural genes include erythropoietin (EPO), vascular endothelial growth hormone (VEGF) and glycolytic genes. HIF-1α migrates on SDS polyacrylamide gel electrophoresis with an apparent molecular mass of 120 kDa and has essentially the amino acid sequence as set forth in SEQ ID NO:1. The term HIF-1α includes the polypeptide as set forth in SEQ ID NO:1, and conservative variations of the polypeptide sequence. The term "conservative variant" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide. In a preferred embodiment, HIF-1α has the sequence as set forth in SEQ ID NO:1. HIF-1α is described in detail in copending application U.S. patent application Ser. No. 08/480,473, now U.S. Pat. No. 5,882,914 herein incorporated by reference.

In general, a mutein will have an amino acid sequence that differs from the native sequence by including substitutions, insertions, and/or deletions for example). Muteins are easily prepared using modem cloning techniques, or may be synthesized by solid state methods by site-directed mutagenesis. A mutein may include dominant negative forms of a polypeptide.

The invention provides a substantially pure stable hypoxia-inducible factor-1α (sHIF-1α) mutein. sHIF-1α polypeptide has a sequence as set forth in SEQ ID NO:1, wherein amino acids 392 to 428 are deleted therefrom, amino acid 551 is changed from a serine to any other amino acid, and amino acid 552 is changed from a threonine to any other amino acid. In one embodiment, amino acids 392 to 428 are deleted from SEQ ID NO:1 and amino acid 551 is changed from a serine to a glycine. In another embodiment, amino acids 392 to 428 are deleted from SEQ ID NO:1 and amino acid 552 is changed from a threonine to an alanine. In yet another embodiment, amino acids 392 to 428 are deleted from SEQ ID NO:1 and amino acid 551 is changed from a serine to a glycine and amino acid 552 is changed from a threonine to an alanine.

Without being bound by theory, two regions of full-length HIF-1α have been identified that are important for stable expression of HIF-1α. Region AB is located from about amino acid 392 to amino acid 552. Within this region, two sequences A and B, have been identified. In particular, sequence A is from amino acid 392 to amino acid 428 of SEQ ID NO:1, and sequence B is at about amino acid 429 to 522 of SEQ ID NO:1. Region C is located from about amino acid 703 to amino acid 726 of SEQ ID NO:1. A "mutation" in SEQ ID NO:1 refers to a deletion, insertion, mutation or substitution of one or more amino acids. Stable HIF-1α can be composed of a mutation or deletion in both regions A and B. Alternatively, stable HIF-1α can be composed of a deletion in region C. For example, regions A and B can be deleted, regions A and B can be mutated, or region A can be mutated and region B can be deleted, region A can be deleted and region B can be mutated, or region C can be mutated, or region C can be deleted. In one nonlimiting example, stable HIF-1α is composed of a deletion of amino acid 392 to amino acid 520 of SEQ ID NO:1. In another nonlimiting example, stable HIF-1α is composed of a deletion of amino acid 392 to 428 of SEQ ID NO:1, combined with point mutation of either amino acid 551 or 552, or combined with point mutation of both amino acid 551 and 552. The point mutation(s) can be combined with a deletion of amino acids 392 to amino acid 428 of SEQ ID NO:1, or the point mutation(s) can be combined with a deletion of amino acid 392 to any amino acid between amino acid 429 and amino acid 550, inclusive, of SEQ ID NO:1.

In yet another nonlimiting example, stable HIF-1α is composed of a deletion of amino acid 704 to amino acid 826 of SEQ ID NO:1. This deletion eliminates the transactivation domain (amino acid 786 to amino acid 826), and thus can result in a loss of biological activity. In one embodiment, stable HID-1α can be formed by deletion of amino acid 704 to amino acid 826 of SEQ ID NO:1, with the addition of a heterologous transactivation domain. The "heterologous" transactivation domain is a transactivation domain derived from a polypeptide other than HIF-1α. In one embodiment, the heterologous transactivation domain is a heterologous transactivation domain that is not affected by oxygen. In one nonlimiting example, the heterologous transactivation domain is a VP16 protein transactivation domain. In this embodiment, deletion of amino acid 391 to 704 is combined with a deletion of amino acid 704 to amino acid 826. A VP16 transactivation domain is then fused to amino acids 1 to amino acid 390 of the HIF-1α polypeptide. Additional combinations of the regions identified to be significant to the formation of sHIF-1α mutein will readily be apparent to one of skill in the art.

A "stable" HIF-1α is an HIF-1α polypeptide which has an increased half-life as compared to wild-type HIF-1α under nonhypoxic conditions. In one embodiment, in a given cell, sHIF-1α has the same half-life under hypoxic or nonhypoxic conditions. In another embodiment, a stable HIF-1α is present at the same concentration in cells exposed to nonhypoxic conditions as in cells exposed to hypoxic conditions.

The ability of wild-type HIF-1α to activate transcription is regulated by oxygen concentration independent of the effect of oxygen on HIF-1α protein stability (Jiang et al., 1997, supra). The region of sHIF-1α located from amino acid 576–785 is a negative regulatory domain that, when deleted, results in increased transcription under nonhypoxic conditions (Jiang et al., *J. Biol. Chem.* 272:19253, 1997, herein incorporated by reference). Thus, without being bound by theory, deletion of one or more amino acids in this sequence, such that the amino acid is replaced by a bond, results in a higher transcription rate, independent of the half life of the protein. Thus, deletion of amino acids 576–785 of HIF-1α can be combined with deletion of amino acids 392–428, and point mutation of amino acid 551 from a serine to a glycine, and point mutation of amino acid 552 from a threonine to an alanine, to yield a stable HIF-1α polypeptide. Deletion of amino acid 576 to amino acid 785 of HIF-1α can also be combined with deletion of amino acids 392 to 520 to yield a stable HIF-1α polypeptide. Alternatively, deletion of amino acid 576 to amino acid 785 of HIF-1α can be combined to deletion of amino acid 704 to amino acid 826 (resulting in deletion of amino acid 576 to 826 of HIF-1α) to yield a stable HIF-1α polypeptide. Such combinations will readily be apparent to one of ordinary skill in the art.

The term "substantially pure" as used herein refers to HIF-1α which is substantially free of other proteins, lipids, carbohydrates or other materials with which it is naturally associated. One skilled in the art can purify HIF-1α using standard techniques for protein purification, such as DNA affinity chromatography (e.g., Wang, G. L., and Semenza, J., *J. Biol. Chem.* 270:1230–1237, 1995) and immunoprecipitation (e.g., Jiang, B. H., et al., *J. Biol. Chem.* 271:17771–17778, 1996). The substantially pure polypeptide will yield a single band on a nonreducing polyacrylamide gel. The purity of the HIF-1α polypeptide can also be determined by amino-terminal amino acid sequence analysis. HIF-1α protein includes functional fragments of the polypeptide, as long as the activity and the stability in nonhypoxic conditions of sHIF-1α remains. Smaller peptides containing the biological activity of sHIF-1α are thus included in the invention.

The invention provides polynucleotide sequences encoding sHIF-1α polypeptide having a sequence as set forth in SEQ ID NO:1, wherein amino acids 392 to 428 are deleted therefrom, amino acid 551 is changed from a serine to any other amino acid, and amino acid 552 is changed from a threonine to any other amino acid. These polynucleotides include DNA, cDNA, and RNA sequences which encode sHIF-1α. It is also understood that all polynucleotides encoding all or a portion of sHIF-1α are also included herein, as long as they encode a polypeptide with HIF-1α activity which is stable under hypoxic and nonhypoxic conditions. Such polynucleotides include naturally occurring, synthetic, and intentionally manipulated polynucleotides. For example, sHIF-1α polynucleotide may be subjected to site-directed mutagenesis. The polynucleotide sequence for sHIF-1α also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of HIF-1α polypeptide is encoded by the nucleotide sequence is functionally unchanged.

Minor modifications of the sHIF-1α primary amino acid sequence may result in proteins which are stable under nonhypoxic conditions and have substantially equivalent activity as compared to the sHIF-1α polypeptide described herein. These minor modifications include the minor differences found in the sequence of HIF-1α polypeptide isolated from different species (e.g., human, mouse, and rat HIF-1α polypeptide). Such proteins include those as defined by the term "having essentially the amino acid sequence" of the sHIF-1α of the invention. Such modifications may be deliberate, as by site-directed mutagenesis, or may be spontaneous, as those found in different species. All of the polypeptides produced by these modifications are included herein as long as the biological activity of sHIF-1α still exists, and the polypeptide is stable under nonhypoxic conditions as compared to wild-type HIF-1α. Further, deletions of one or more amino acids can also result in modification of the structure of the resultant molecule without significantly altering its biological activity. This can lead to the development of a smaller active molecule which would have broader utility. For example, one can remove amino or carboxy terminal amino acids which are not required for sHIF-1α biological activity.

Specifically disclosed herein is a DNA sequence encoding the human sHIF-1α mutein. The invention provides polynucleotide sequences encoding stable HIF-1α mutein having a sequence as set forth in SEQ ID NO:1, wherein amino acids 392 to 428 are deleted therefrom, amino acid 551 is changed from a serine to any other amino acid, and amino acid 552 is changed from a threonine to any other amino acid. The wild type HIF-1α contains an open reading frame encoding a polypeptide 826 amino acids in length. When amino acid 551 (serine) of SEQ ID NO:1 is replaced by another amino acid, such as an glycine, or amino acid 552 (threonine) of SEQ ID NO:1 is replaced by another amino acid, such as alanine, and one or more of amino acid 392 to amino acid 429 of SEQ ID NO:1 is replaced by a bond, the polynucleotide will encode a polypeptide that is decreased in length by a corresponding number of amino acids.

In another embodiment, the invention provides polynucleotides encoding sHIF-1α as well as nucleic acid sequences complementary to polynucleotides encoding sHIF-1α. The term "polynucleotide" or "nucleic acid sequence" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double stranded forms of DNA.

A complementary sequence may include an antisense nucleotide. When the sequence is RNA, the deoxynucleotides A, G, C, and T in the polynucleotide encoding sHIF-1α are replaced by ribonucleotides A, G, C, and U, respectively, Also included in the invention are fragments of the above-identified nucleic acid sequences that are at least bases in length, which is sufficient to permit the fragment to selectively hybridize to nucleic acid that encodes sHIF-1α, but not SEQ ID NO:1 under physiological conditions. Specifically, the fragments should selectively hybridize to nucleic acid encoding sHIF-1α polypeptide. The term "selectively hybridize" refers to hybridization under moderately or highly stringent conditions which excludes non-related nucleotide sequences.

In nucleic acid hybridization reactions, the conditions used to achieve a particular level of stringency' will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

When using an sHIF-1α specific probe, it may be necessary to amplify the nucleic acid prior to binding with an sHIF-1α specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

The sHIF-1α polynucleotide of the invention can be derived from a mammalian organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequences must be known. The DNA sequence encoding the protein can be deduced from the genetic code, however, the degeneracy of the code must be taken into account. In a preferred embodiment, the probe can delineate between sHIF-1α and wild-type HIF-1α.

It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid nonspecific binding, it is possible, for example, to allow the autoradiographic visualization of a specific cDNA clone by the hybridization of the target DNA to that single probe in the mixture which is its complete complement (Sambrook et al., *Molecular Cloning: A Laboratory Manual* 2nd Ed.; Cold Spring Harbor Laboratory Press, Plainview, N.Y., 1998).

The development of specific DNA sequences encoding sHIF-1α can also be obtained by site-directed mutagenesis of a nucleic acid sequence encoding SEQ ID NO:1 or chemical manufacture of a DNA sequence to provide the necessary codons for the polypeptide of interest. The synthesis of DNA sequences is frequently the method of choice when the entire sequence of amino acid residues of the desired polypeptide product is known.

A cDNA expression library, such as in phage lambda gt11, can be screened indirectly for sHIF-1α peptides having at least one epitope, using antibodies specific for sHIF-1α. Such antibodies can be either polyclonally or monoclonally derived and used to detect expression product indicative of the presence of sHIF-1α cDNA.

DNA sequences encoding sHIF-1α can be expressed in vitro by DNA transfer into a suitable host cell. "Host cells" are cells in which a vector can be propagated and its DNA expressed. Host cells include both prokaryotic and eukaryotic cells. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

"Modified" versions of the specific sHIF-1α can be engineered to further enhance stability, biological acitvity, production, purification, or yield of the expressed product. For example, the expression of a fusion protein or a cleavable fusion protein comprising the sHIF-1α and a heterologous protein can be engineered. Such a fusion protein can be readily isolated by affinity chromatography, e.g., by immobilization on a column specific for the heterologous protein. Where a cleavage site is engineered between the HIF-1α moiety and the heterologous protein, the HIF-1α polypeptide can be released from the chromatographic column by treatment with an appropriate enzyme or agent that digests at the cleavage site (Booth et al., *Immunol. Lett.* 19:65–708, 1988; Gardella et al., *J. Biol. Chem.* 265:15854–15859, 1990).

In the present invention, the sHIF-1α polynucleotide sequences may be inserted into an expression vector. The term "expression vector" refers to a plasmid, virus or other vehicle known in the art that has been manipulated by insertion or incorporation of the sHIF-1α genetic sequences. Polynucleotide sequence which encode sHIF-1α can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, as start codon (i.e., ATG) in front of a protein-encoding gene, splicing signal for introns, maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., *Methods in Enzymology* 153:516–544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein or elongation factor-1α promoter) or from mammalian viruses (e.g., the retrovirus long terminal repeat; the adenovirus late promoter; the vaccinia virus 7.5K promoter; the cytomegalovirus promoter) may be used. Promoters produced by recombinant DNA or synthetic techniques may also be used to provide for transcription of the nucleic acid sequences of the invention.

In the present invention, the polynucleotide encoding sHIF-1α may be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

In yeast, a number of vectors containing constitutive or inducible promoters may be used. For a review see, *Current Protocols in Molecular Biology,* Vol. 2, Ch. 3, Ed. Ausubel et al., Greene Publish. Assoc. & Wiley Interscience, 1988; Grant et al., "Expression and Secretion Vectors for Yeast," in *Methods in Enzymology,* Vol. 153, pp. 516–544, Eds. Wu & Grossman, 31987, Acad. Press, N.Y., 1987; Glover, *DNA Cloning,* Vol. II, Ch. 3, IRL Press, Wash., D.C., 1986; and Bitter, "Heterologous Gene Expression in Yeast," *Methods in Enzymology,* Vol. 152, pp. 673–684, Eds. Berger & Kimmel, Acad. Press, N.Y., 1987; and *The Molecular Biology of the Yeast Saccharomyces,* Vols. I and II, Eds. Strathern et al., Cold Spring Harbor Press, 1982. A constitutive yeast promoter such as ADH or LEU2 or an inducible promoter such as GAL may be used ("Cloning in Yeast," R. Rothstein In: *DNA Cloning, A Practical Approach,* Vol. 11, Ch. 3, Ed. D. M. Glover, IRL Press, Wash., D.C., 1986). Alternatively, vectors may be used which promote integration of foreign nucleic acid sequences into the yeast chromosome.

Mammalian expression systems which utilize recombinant viruses or viral elements to direct expression may be engineered. For example, when using adenovirus expression vectors, the sHIF-1α coding sequence may be ligated to an adenovirus transcription/translation control complex, e.g., the late promoter and tripartite leader sequence. Alternatively, the vaccinia virus 7.5K promoter may be used. (e.g., see, Mackett et al., *Proc. Natl. Acad. Sci. USA* 79:7415–7419, 1982; Mackett et al., *J. Virol.* 49:857–864, 1984; Panicali et al., Proc. Natl. Acad. Sci USA 79:4927–4931, 1982). Of particular interest are vectors based on bovine papilloma virus which have the ability to replicate as extrachromosomal elements (Sarver, et al., *Mol. Cell. Biol.* 1:486, 1981). Shortly after entry of this nucleic acid into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the sHIF-1α gene in host cells (Cone & Mulligan, *Proc. Natl. Acad. Sci. USA* 81:6349–6353, 1984). High level expression may also be achieved using inducible promoters, including, but not limited to, the metallothionein IIA promoter and heat shock promoters.

Polynucleotide sequences encoding sHIF-1α can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

For long-term, high-yield production of recombinant proteins, stable expression is preferred. Rather than using expression vectors which contain viral origins of replication, host cells can be transformed with sHIF-1α cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign nucleic acid, engineered cells may be allowed to grow for 1–2 days in an enriched media, and then are switched to a selective media. A number of selection systems may be used, including, but not limited to the herpes simplex virus thymidine kinase gene (Wigler, et al., *Cell* 11:223, 1977), hypoxanthine-guanine phosphoribosyltransferase gene (Szybalska & Szybalski, *Proc. Natl. Acad. Sci. USA* 48:2026, 1962), and the adenine phosphoribosyltransferase (Lowy, et al., *Cell* 22:817, 1980) genes can be employed in tk-, hgprt⁻ or aprt⁻ cells respectively. Additionally, antimetabolite resistance can be used as the basis of selection for dhfr, which confers resistance to methotrexate (Wigler, et al., *Natl. Acad. Sci. USA* 77:3567, 1980; O'Hare, et al., *Proc. Natl. Acad. Sci. USA* 78:1527, 1981); the gpt gene, which confers resistance to mycophenolic acid (Mulligan & Berg, *Proc. Natl. Acad. Sci. USA* 78:2072, 1981; the neo gene, which confers resistance to the aminoglycoside G-418 (Colberre-Garapin, et al., *J. Mol Biol.* 150:1, 1981); and the hygro gene, which confers resistance to hygromycin (Santerre, et al., *Gene* 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047, 1988); and ODC (ornithine decarboxylase) which confers resistance to the ornithine decarboxylase inhibitor, 2-(difluoromethyl)-DL-ornithine, DFMO (McConlogue L., In: *Current Communications in Molecular Biology,* Cold Spring Harbor Laboratory ed., 1987).

By "transformation" is meant a genetic change induced in a cell following incorporation of new DNA (i.e., DNA exogenous to the cell). Where the cell is a mammalian cell, the genetic change is generally achieved by introduction of the DNA into the genome of the cell (i.e., stable).

By "transformed cell" is meant a cell into which (or into an ancestor of which has been introduced, by means of recombinant DNA techniques, a DNA molecule encoding sHIF-1α. Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the CaCl$_2$ method using procedures well known in the art.

Alternatively, MgCl$_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the sHIF-1α of the invention, and a second foreign DNA molecule encoding a selectable phenotype, such as the herpes simplex thymidine kinase gene. Another method is to use a eukaryotic viral vector, such as simian virus 40 (SV40), adenovirus, or bovine papilloma virus, to transiently infect or transform eukaryotic cells and express the protein (see for example, *Eukaryotic Viral Vectors,* Cold Spring Harbor Laboratory, Gluzman, ed., 1982).

Isolation and purification of microbial expressed polypeptide, or fragments thereof, provided by the invention, may be carried out by conventional means including preparative chromatography and immunological separations involving monoclonal or polyclonal antibodies.

ANTIBODIES

The HIF-1α polypeptides of the invention can also be used to produce antibodies which are immunoreactive or selectively bind to epitopes of the sHIF-1α polypeptides. An antibody which "selectively binds" to sHIF-1α is an antibody that binds sHIF-1α with a higher affinity the antibody binds to wild-type HIF-1α. Thus, antibodies of the invention can be used to distinguish the presence of sHIF-1α mutein from wild-type HIF-1α polypeptide. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler et al. *Nature* 256:495, 1975; *Current Protocols in Molecular Biology,* Ausubel et al., ed., 1989).

The term "antibody" as used in this invention includes intact molecules as well as fragments thereof, such as Fab, F(ab')2, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. See, for example, Harlow and Lane, *Antibodies: A Laboratory Manual,* Cold Spring Harbor Laboratory, New York, 1988, incorporated herein by reference.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which selectively bind to the sHIF-1α polypeptide of the invention, can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies. See, for example, Coligan et al., Unit 9, *Current Protocols in Immunology,* Wiley Interscience, 1994, herein specifically incorporated by reference.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

For purposes of the invention, an antibody or nucleic acid probe specific for sHIF-1α may be used to detect sHIF-1α polypeptide or polynucleotide in biological fluids, cultured cells or tissues. The antibody reactive with sHIF-1α or the nucleic acid probe is preferably labeled with a compound which allows detection of binding to sHIF-1α. Any specimen containing a detectable amount of antigen or polynucleotide can be used.

THERAPEUTIC INTERVENTION

The invention provides methods for treatment of HIF-1-mediated disorders, including hypoxia-mediated tissue damage, which are improved or ameliorated by modulation of HIF-1 gene expression or activity. The term "modulate" envisions the induction or augmentation of HIF-1 expression when appropriate. The term "ameliorate" denotes a lessening of the detrimental effect of the associated disease in the subject receiving therapy. Where expression or augmentation of expression of HIF-1 is desirable, the method of the treatment includes administration of substantially purified sHIF-1α polypeptide or polynucleotide.

According to the method of the invention, substantially purified sHIF-1α mutein or the polynucleotide sequence encoding sHIF-1α is introduced into a human patient for the treatment or prevention of HIF-1-mediated disorders. The appropriate human patient is a subject suffering from a HIF-1-mediated disorder, such as an ischemic disease, or a hypoxia-related disorder (for example, coronary, cerebral, or peripheral arterial disease).

The present invention provides the introduction of polynucleotides encoding sHIF-1α for the treatment of hypoxia-related disorders, which are improved or ameliorated by expression of the HIF-1α polypeptide. Such therapy would achieve its therapeutic effect by introduction of the sHIF-1α polynucleotide into cells exposed to hypoxic conditions. HIF-1α is thus expressed in both the hypoxic and surrounding nonhypoxic tissues, such that it can dimerize with HIF-1β (which is present in excess in hypoxic and nonhypoxic cells), and activate the transcription of downstream target genes. Examples of genes which can be activated by HIF-1 are vascular endothelial growth factor, glucose transporters, and glycolytic enzymes. These genes mediate important adaptive responses to hypoxia including angiogenesis and glycolysis.

Delivery of sHIF-1α polynucleotide can be achieved using a recombinant expression vector such as a chimeric virus or a colloidal dispersion system. Especially preferred for therapeutic delivery of sequences is the use of targeted liposomes.

Various viral vectors which can be utilized for gene therapy as taught herein include adenovirus, adeno-associated virus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a sHIF-1α sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the sHIF-1α polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for HIF-1 polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LW), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley et al., *Trends Biochem. Sci.* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al. *Biotechniques* 6:682, 1988).

The composition of the liposome is usually a combination of phospholipids, particularly high-phase-transition-temperature phospholipids, usually in combination with sterols, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidyl-glycerol, phosphatidylcholine, phosphatidylserine, phosphatidylethanolamine, sphingolipids, cerebrosides, and gangliosides. Particularly useful are d-iacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

sHIF-1α polypeptide can be used in therapeutic administration. For such administration the polypeptide must be sterile. Sterility is readily accomplished by sterile filtration through (e.g., 0.2 micron) membranes. The compound of the invention ordinarily will be stored as unit or multidose containers, for example, sealed ampules or vials, as an aqueous solution, as it is highly stable to thermal and oxidative denaturation. Lyophilized formulations for reconstitution are also acceptable. The polypeptide will be administered as a pharmaceutical composition (see below).

The invention also describes a method of treating a subject having a hypoxia related disorder by administering to the subject a therapeutically-effective amount of cells expressing sHIF-1α. "Therapeutically-effective" as used herein, refers to that amount of cells that is of sufficient quantity to alleviate a symptom of the disease or to ameliorate the hypoxia-related disorder. Transduction of the cell is performed in vitro, generally with isolated cell populations or cell lines. The cells may be xenogeneic, allogeneic, syngeneic or autologous, preferably autologous, in order to reduce adverse immune responses. The cells may be administered in any physiologically acceptable medium, normally intravascularly, although they may also be introduced into tissue surrounding a vessel or other convenient site, where the cells may find an appropriate site for expansion and differentiation. "Ameliorate" refers to lessening or lowering the disease's or disorder's detrimental effect in the patient receiving the therapy.

Any of the transplantation or implantation procedures known in the art can be utilized. For example, the selected cells or cells of interest can be surgically implanted into the recipient or subject. Transplantation or implantation is typically by simple injection through a hypodermic needle having a bore diameter sufficient to permit passage of a suspension of cells therethrough without damaging the cells or tissue coating. For implantation, the typically encapsulated or coated cells are formulated as pharmaceutical compositions together with a pharmaceutically-acceptable carrier. Such compositions contain a sufficient number of coated transplant cells which can be injected into, or administered through a laparoscope to, a subject. Usually, at least about $1 \times 10^4$ to $1 \times 10^5$ cells will be administered, preferably $1 \times 10^6$ or more. The cells may be frozen at liquid nitrogen temperatures and stored for long periods of time, being capable of use on thawing. Once thawed, the cells may be expanded. Further, the cells can be administered in an encapsulated form or non-encapsulated form. Preferably the cells are encapsulated.

While not required, it may be desirable to administer an immunosuppressive agent to a recipient of the cells, prior to, simultaneous with, and/or after transplantation. In particular, an immunosuppressive agent can be utilized with xenogeneic or allogeneic cells expressing sHIF-1α. An agent such as Cyclosporine A (CsA) is preferable, however other immune suppressive agents can be used, such as rapamycin, desoxyspergualine, FK506 and like. These agents are administered to cause an immunosuppressive effect in the subject, such that the transplanted cells are not rejected by that subject's immune system. Typically, the immunosuppressive agent is administered continuously through-out the transplant treatment typically over a period of days or weeks; for example, CsA treatment ranges from about 2 to about 20 days at a dosage range of about 5 to 40 mg per kilogram of body weight per day. The agent can be administered by a variety of means, including parenteral, subcutaneous, intrapulmonary, oral, intranasal administration and the like. Preferably, dosing is given by oral administration.

The cells expressing HIF-1α also can be encapsulated prior to transplantation. Although the cells are typically microencapsulated, they can be encased in various types of hollow fibers or in a block of encapsulating material. A variety of microencapsulation methods and compositions are known in the art. A number of microencapsulation methods for use in transplant therapy have focused on the use of alginate polymers or agarose to supply the encapsulation compositions. Alginates are linear polymers of mannuronic and guluronic acid residues which are arranged in blocks of several adjacent guluronic acid residues forming guluronate blocks and block of adjacent mannuronic acid residues forming mannuronate blocks, interspersed with mixed, or heterogenous blocks of alternating guluronic and mannuronic acid residues. Generally, monovalent cation alginate salts are soluble, e.g., Na-alginate.

Divalent cations, such as $Ca^{++}$, $Ba^{++}$ or $Sr^{++}$, tend to interact with guluronate, and the cooperative binding of these cations within the guluronate blocks provides the primary intramolecular crosslinking responsible for formation of stable ion-paired alginate gels. Alginate encapsulation methods generally take advantage of the gelling of alginate in the presence of these divalent cation solutions. In particular, these methods involve the suspension of the material to be encapsulated, in a solution of monovalent cation alginate salt, e.g., sodium. Droplets of the solution are then generated in air and collected in a solution of divalent cations, e.g., $CaCl_2$. The divalent cations interact with the alginate at the phase transition between the droplet and the divalent cation solution resulting in the formation of a stable alginate gel matrix being formed. Generation of alginate droplets has previously been carried out by a number of methods. For example, droplets have been generated by extrusion of alginate through a tube by gravitational flow, into a solution of divalent cations. Similarly, electrostatic droplet generators which rely on the generation of an electrostatic differential between the alginate solution and the divalent cation solution have been described. The electrostatic differential results in the alginate solution being drawn through a tube, into the solution of divalent cations. Methods have been described wherein droplets are generated from a stream of the alginate solution using a laminar air flow extrusion device. Specifically, this device comprises a capillary tube within an outer sleeve. Air is driven through the outer sleeve and the polymer solution is flow-regulated through the inner tube. The air flow from the outer sleeve breaks up the fluid flowing from the capillary tube into small droplets (see U.S. Pat. No. 5,286,495). For a general discussion of droplet generation in encapsulation processes, see, e.g., M. F. A. Goosen, Fundamentals of Animal Cell Encapsulation and Mobilization, Ch. 6, pp. 114–142 (CRC Press, 1993).

Attempts to transplant organ tissues into genetically dissimilar hosts without immunosuppression are generally defeated by the immune system of the host. Accordingly, attempts have been made to provide other effective protective barrier coatings, e.g., by microencapsulation, to isolate the transplant tissues from the host immune system. Successful cell or tissue transplants generally require a coating that will prevent their destruction by a host's immune system, prevent fibrosis, and will be permeable to and allow a free diffusion of the nutrients to the coated transplant and removal of the secretory and waste products from the coated transplant. Viable tissue and cells have been successfully immobilized in alginate capsules coated with polylysine (see above and *J. Pharm. Sci.* 70:351–354, 1981). The development of transplants encapsulated in calcium alginate capsules reacted with polylysine is also described, for example, in U.S. Pat. Nos. 4,673,566, 4,689,293, 4,789,550, 4,806, 355, and 4,789,550. U.S. Pat. No. 4,744,933 describes encapsulating solutions containing biologically active materials in a membrane of inter-reacted alginate and polyamino acid. U.S. Pat. No. 4,696,286 reports a method for coating transplants suitable for transplantation into genetically dissimilar individuals. The method involves coating the transplant with a surface conforming bonding bridge of a multifunctional material that binds chemically to a surface component of the transplant, which is enveloped in a semipermeable, biologically compatible layer of a polymer that binds chemically to the bonding bridge layer. A method for introducing a second alginate gel coating to cells already coated with polylysine alginate is described in U.S. Pat. No. 5,227,298. Both the first and second coating of this method require stabilization by polylysine.

Encapsulation methods applied to make these materials have comprised a procedure for forming droplets of the encapsulating medium and the biological material and a procedure for solidifying the encapsulating medium. Agarose encapsulated materials have been formed by chilling an emulsion of agarose droplets containing biological materials as shown by Nilsson, et al., *Nature* 302:629–630 (1983) and Nilsson, et al., *Eur. J Appl. Microbiol. B-iotechnol.* 17:319–326 (1983). Injection of droplets of polymer containing biological materials into a body of coolant such as concurrently liquid stream has been reported by Gin, et al., *J. Microencapsulation* 4:329–242 (1987).

PHARMACEUTICAL COMPOSITIONS

This invention involves administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, orally, intravenously, or by another parenteral route, or as implants, or even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science,* 249:1527–1533, 1990, which is incorporated herein by reference.

For delivery of sHIF-1α mutein, the formulations are prepared by contacting sHIF-1α mutein uniformly and intimately with liquid carriers or finely divided solid carriers or both, and then, if necessary, shaping the product into the desired formulation. Preferably the carrier is a parenteral carrier, more preferably a solution that is isotonic with the blood of the recipient. Examples of such carrier vehicles include water, saline, Ringer's solution, dextrose solution, and 5% human serum albumin. Nonaqueous vehicles such as fixed oils and ethyl oleate are also useful herein, as well as liposomes. Generally, the carrier can contain minor amounts of additives such as substances that enhance isotonicity and chemical stability, e.g., buffers and preservatives, as well as low molecular weight (less than about 10 residues) polypeptides, proteins, amino acids, carbohydrates including glucose or dextrans, chelating agents such as EDTA, or other excipients.

The composition herein is also suitably administered by sustained release systems. Suitable examples of sustained release compositions include semipermeable polymer matrices in the form of shaped articles, e.g., films, microcapsules, or microspheres. Sustained release matrices include, for example, polyactides (U.S. Pat. No. 3,773,919), copolymers of L-glutamic acid and γ-ethyl-L-glutamate (Sidman et al., *Biopolymers* 22:547–556, 1983), or poly-D-(-)-3-hydroxybutyric acid (EP 133,988). Sustained release compositions also include one or more liposomally entrapped compounds of formula I. Such compositions are prepared by methods known per se, e.g., as taught by Epstein et al. *Proc. Natl. Acad. Sci. USA* 82:3688–3692, 1985. Ordinarily, the liposomes are of the small (200–800 Å) unilamellar type in which the lipid content is greater than about 30 mol % cholesterol, the selected proportion being adjusted for the optimal therapy.

The pharmaceutical compositions according to the invention may be administered locally or systemically. By "therapeutically effective dose" is meant the quantity of a compound according to the invention necessary to prevent, to cure or at least partially arrest the symptoms of the disorder and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman And Gilman's: The Pharmacological Bases of Therapeutics,* 8th ed., Pergamon Press, 1990; and *Remington's Pharmaceutical Sciences,* 17th ed., Mack Publishing Co., Easton, Pa., 1990; each of which is herein incorporated by reference.

The following examples are intended to illustrate but not limit the invention. While they are typical of those that might be used, other procedures known to those skilled in the art may alternatively be used.

EXAMPLE 1

Generation of a Constitutively Expressed Form of HIF-1α

It has previously been shown (Jiang et al., *J. Biol. Chem* 272:19253, 1997; Pugh et al., *J. Biol. Chem.* 272:11205) that a fusion protein consisting of the GAL4 DNA binding domain fused to HIF-1α residues 531–826 is a constitutively expressed protein that can activate transcription of reporter genes containing GAL4 binding sites. However, these GAL4/HIF-1α constructs do not activate the normal target genes regulated by HIF-1. To generate a constitutively expressed form of HIF-1α, two series of deletion constructs were produced, one in which the deletions began at the carboxyl-terminal end of the molecule (amino acid 826) and extended towards the amino terminus, and one in which the deletions began at amino acid 392 and extended towards the carboxyl terminus.

Each of these constructs was expressed in mammalian cells under nonhypoxic (20% $O_2$) or hypoxic (1% $O_2$) conditions, and the expression of endogenous full length HIF-1α and transfected deleted HIF-1α was quantitated by immunoblot assay using affinity-purified anti-HIF-1α antibodies. These studies revealed that endogenous HIF-1α showed regulated expression (more protein expressed in cells at 1% $O_2$ than in cells at 20% $O_2$). In addition the studies showed that C-terminal deletion to amino acid 726 had no effect on the regulation of HIF-1α protein expression by $O_2$ concentration, whereas deletion to amino acid 703 or beyond resulted in loss of regulation (i.e., constitutive expression, see FIG. 2). Internal deletions extending from amino acid 392 through 517 had no effect on expression, whereas deletion of amino acid 392 to amino acid 521 resulted in loss of regulation (see FIG. 3). In addition, the missense mutations S551G/T552A (a serine to glycine and threonine to alanine substitution at amino acid 551 and 552, respectively) resulted in loss of regulation of the internal deletion constructs that otherwise showed regulation (i.e., deletions extending from amino acid 392 to anywhere between amino acid 429 and 517). These missense mutations alone did not cause dysregulated expression of full-length HIF-1α (amino acids 1–826, see FIG. 3).

The results suggested that there were two regions of HIF-1α that were required for regulated expression, such that deletion of either region resulted in dysregulated expression (see FIG. 4). The first of these regions is region AB (amino acid 392–552). Within this internal region, two sequences (A and B) were identified that appeared functionally redundant, since the presence of either sequence was sufficient for regulation. One of these sequences (A) was identified by the 392–428 deletion and the other sequence (B) was identified by the 392–520 deletion, or the S551G/T552A point mutations. This latter result suggested that the serine and/or threonine residue was subjected to phosphorylation/dephosphorylation which could be disrupted by the 392–520 deletion. Since loss of the serine/threonine sequence mimicked hypoxia, these results suggest phosphorylation of serine 551 and/or threonine 552 under nonhypoxic conditions and dephosphorylation under hypoxic conditions. Based upon the redundancy of A and B, it is possible that a phosphatase may also bind at the A site and dephosphorylate a nearby serine or threonine reside.

Region C is defined by the different effects of deletions encompassing amino acids 704 to 826 as compared to deletions encompassing amino acids 727 to 826. Loss of region C is not redundant with the loss of region AB, thus it is likely that this region will be involved in some other function related to regulation of HIF-1α stability. Without being bound by theory, it is possible this region is involved in ubiquitination or proteolysis.

Figure 5:
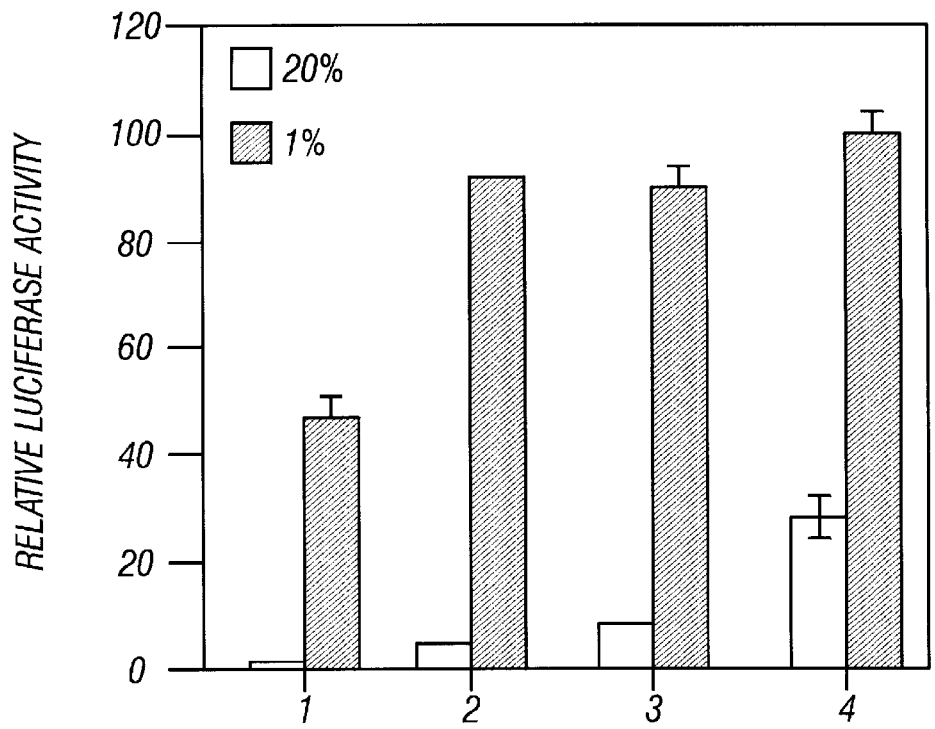
FIG. 5 is a bar graph illustrating the luciferase activity upon cotransfection of 293 cells with a reporter gene containing a hypoxic response element (that includes a HIF-1 binding site) with expression vector pCEP4 encoding (1) no protein; (2) full-length HIF-1α (amino acis 1–826); (3) HIF-1α (1–391/429–826, deletion only); (4) HIF-1αDP (deletion and a serine to glycine mutation at amino acid 551 and a threonine to alanine mutation at residue 552). Reporter gene expression is shown at 1% (black bars) and 20% $O_2$ (white bars).
Figure 6:
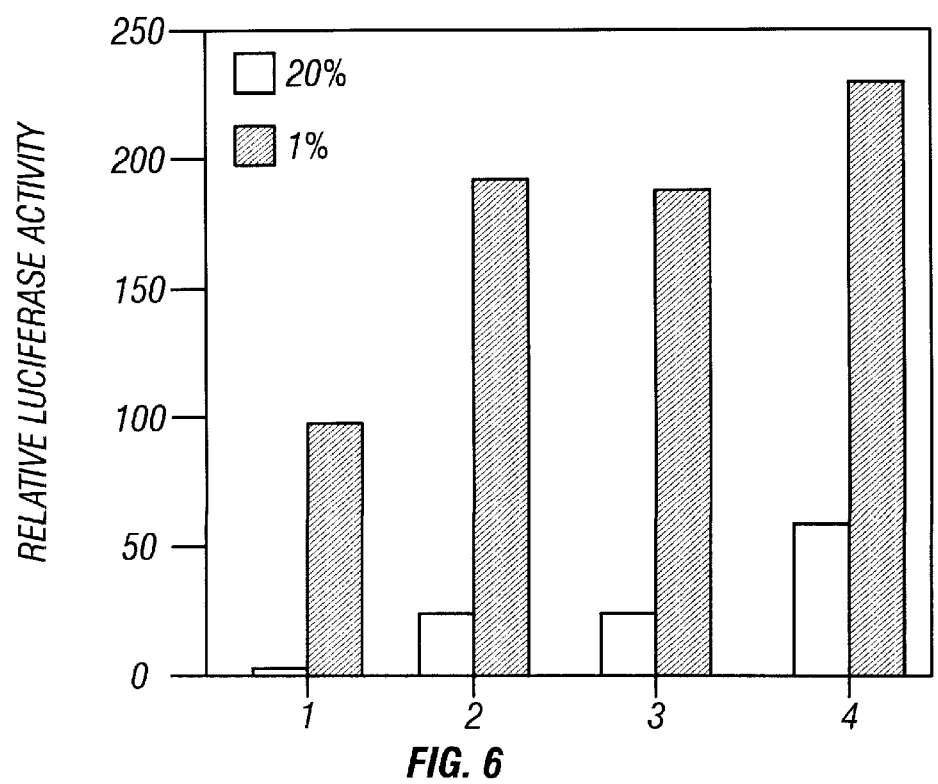
FIG. 6 is a bar graph illustrating the luciferase activity upon cotransfection of Hep3B cells with a reporter gene containing a hypoxic response element (that includes a HIF-1 binding site) and with expression vector pCEP4 encoding (1) no protein; (2) HIF-1α; (3) HIF-1α (1–391/429–826, deletion only); (4) HIF-1αDP (deletion and a serine to glycine mutation at amino acid 551 and a threonine to alanine mutation at residue 552). Reporter gene expression is shown at 1% (black bars) and 20% $O_2$ (white bars).

A powerful transactivation domain is located between amino acids 786 and 826. As a result, although HIF-1α (amino acid 1–703) is constitutively expressed, it is not as biologically active as full-length HIF-1α. In order to determine if sHIF-1α would demonstrate increased biological activity compared to full-length HIF-1α cotransfection experiments using the deletion/point mutant HIF-1α (1–391/512–826/S551G/T552A), a stable HIF-1α, were performed. Either 293 cells (see FIG. 5) or Hep3B cells (see FIG. 6) were cotransfected with a reporter gene containing a hypoxia response element that includes an HIF-1 binding site, and with mammalian expression vector pCEP4 (Invitrogen) encoding either (1) no protein, (2) HIF-1α (1–826), (3) HIF-1α (1–391/429–826) (deletion only), or (4) stable HIF-1α (HIF-1αDP, a form of sHIF-1α which contains 1–391/512–826/S551G/T552A). Endogenous HIF-1β is constitutively expressed in these cells at levels in excess of HIF-α expression. In both cell types, HIF-1αDP (sHIF-1α) mediated significantly greater reporter gene expression in cells exposed to 20% $O_2$, due to the presence of higher levels of biologically active HIF-1α (note that HIF-1α is normally expressed only at 1% $O_2$). These results demonstrate a constitutively-expressed and biologically active form of HIF-1α has been generated.

Although the invention has been described with reference to the presently preferred embodiments, it should be understood that various modifications can be made without departing from the spirit of the invention. Accordingly, the invention is limited only by the following claims.

What is claimed is:

1. A substantially purified hypoxia inducible factor-1 (HIF-1), having a sequence comprising amino acid residues 1–391 and 429–826 of SEQ ID NO: 2; amino acid residues 1–391 and 469–826 of SEQ ID NO:2; amino acid residues of 1–391 and 494–826 of SEQ ID NO: 2; amino acid residues 1–391 and 508–826 of SEQ ID NO: 2; amino acid residues 1–391 and 512–826 of SEQ ID NO:2; or amino acid residues 1–391 and 517–826 of SEQ ID NO:2, wherein amino acid 551 is changed from a serine to any other amino acid, and amino acid 552 is changed from a threonine to any other amino acid.

2. The hypoxia inducible factor-1 of claim 1, wherein amino acid 551 is a glycine.

3. The hypoxia inducible factor-1 of claim 1, wherein amino acid 552 is an alanine.

4. The hypoxia inducible factor-1 of claim 1, further comprising a deletion of amino acids 576–785.

5. An isolated nucleic acid sequence encoding a human hypoxia inducible factor-1 (HIF-1) of claim 1.

6. The nucleic acid of claim 5, further comprising an expression control sequence operatively linked to a nucleic acid encoding a hypoxia inducible factor-1 (HIF-1).

7. The nucleic acid sequence of claim 6, wherein the expression control sequence is a promoter.

8. The nucleic acid sequence of claim 7, wherein the promoter is tissue specific.

9. An expression vector containing the polynucleotide of claim 5.

10. The vector of claim 9, wherein the vector is a plasmid.

11. The vector of claim 9, wherein the vector is a viral vector.

12. The vector of claim 11, wherein the vector is a retroviral vector.

13. An isolated host cell containing the vector of claim 9.

14. An isolated host cell of claim 13, wherein the cell is a eukaryotic cell.

15. An isolated host cell of claim 13, wherein the cell is a prokaryotic cell.

16. An antibody which selectively binds to the polypeptide of claim 1.

17. The antibody of claim 16, wherein the antibody is monoclonal.

18. The antibody of claim 16, wherein the antibody is polyclonal.

* * * * *